United States Patent [19]

Matsumura et al.

[11] Patent Number: 5,342,779
[45] Date of Patent: Aug. 30, 1994

[54] PHOTOCHEMICALLY ENHANCED MICROBIAL DEGRADATION OF ENVIRONMENTAL POLLUTANTS

[75] Inventors: Fumio Matsumura, Davis, Calif.; Arata Katayama, Chikusa, Japan

[73] Assignee: The Regents of the University of California, Oakland, Calif.

[21] Appl. No.: 687,368

[22] Filed: Apr. 18, 1991

[51] Int. Cl.$^5$ .................... B09B 3/00; D06M 16/00; C12N 1/14; C12N 13/00
[52] U.S. Cl. ................. 435/262.5; 435/262; 435/254.1; 435/173.8; 435/312; 588/207
[58] Field of Search ............ 435/262, 262.5, 821, 435/312, 173, 173.8, 254.1, 911; 588/207

[56] References Cited

PUBLICATIONS

Samson et al. Sciences et Techniques de l'eau vol. 23. No. 1 (Feb., 1990) pp. 15–23. (English Translation attached).
Yin et al. Biosis Abstract of Journal of Biotechnology vol. 10 No. 1 (1989) pp. 77–84.
Thomas, J. M., et al., "In situ biorestoration of organic contaminants in the subsurface," *Environ. Sci. Technol.*, 23(7):760–766 (1989).
Daley, P. S., "Cleaning up sites with on-site process plants," *Environ. Sci. Technol.*, 23(8):912–916 (1989).
Easty, D. B., et al., "Determination of polycholorinated biphenyls in paper mill effluents," *Tappi*, 61(10):71–74 (Oct. 1978).
Alexander, M., "Biodegradation of Chemicals of Environmental Concern," *Science*, 211:132–138 (Jan. 9, 1981).
Rappe, C., "Analysis of polychlorinated dioxins and furans," *Environ. Sci. Technol.*, 18(3):78A–90A (1984).
Bumpus, J. A., et al., "Oxidation of Persistent Envirnomental Pollutants by a White Rot Fungus," *Science*, 228:1434–1436 (1985).

Aust, S. D., "Biodegradation of Agrochemicals by White Rot Fungi," In *Recent Advances in Microbial Ecology*, 529–533 (1989).
Eaton, D. C., "Mineralization of polychlorinated biphenyls by Phanerochaete chrysosporium: a ligninolytic fungus,"*Enzyme Microb. Technol.*, 7:194–196 (May, 1985).
Huynh, V., et al, "Dechlorination of chloro–organics by a white–rot fungus," *Tappi Journal*, 68:98–102 (Jul. 1985).
Mileski, G. J., et al., "Biodegradation of Pentachlorophenol by the White Rot Fungus Phanerochaete chrysosporium," *Applied and Environmental Microbiology*, 54(12):2885–2889 (Dec. 1988).
Hammel, K. E., et al., "Oxidation of Polycyclic Aromatic Hydrocarbons and Dibenzo[p]–dioxins by Phanerochaete chrysosporium Ligninase,"*J. of Biol. Chem.*, 261(36):16948–16952 (Dec. 25, 1986).

(List continued on next page.)

*Primary Examiner*—Michael G. Wityshyn
*Assistant Examiner*—T. J. Reardon
*Attorney, Agent, or Firm*—Townsend and Townsend Khourie and Crew

[57] ABSTRACT

This invention provides for improved methods of biodegradation of environmental pollutants. The invention specifically provides for the simultaneous treatment of the pollutants in a contaminated medium with ultraviolet radiation and lignin-degrading fungi. The preferred fungus is the white rot fungus *Phanerochaete chrysosporium* ATCC 64046. The fungi are discontinuously contacted with the mass of a contaminated medium. When removed from the mass of contaminated medium, the fungi and adhering contaminated medium are simultaneously exposed to the ultraviolet radiation. The combination of fungal enzymes and ultraviolet radiation enhances the rates of degradation beyond that expected for either of the treatments alone.

11 Claims, 5 Drawing Sheets

PUBLICATIONS

Bumpus, J. A., "Biodegradation of Polycyclic Aromatic Hydrocarbons by Phanerochaete chrysosporium,"*Appl. & Environ. Microbiol.*, 55(1):154–158 (Jan., 1989).

Eaton, D., et al., "Fungal decolorization of kraft bleach plant effluents," *Tappi,* 63(10):103–106 (Oct. 1980).

Eaton, D. C., et al., "Method obtains fungal reduction of the color of extraction-stage kraft bleach effluents," *Tappi,* 65(6):89–92 (Jun., 1982).

Kirk, T. K., et al., "Enzymatic 'Combustion': The Microbial Degradation of Lignin," *Ann. Rev. Microbiol.,* 41:465–505 (1987).

Zabik, M. J., et al., "Photochemistry of Bioactive Compounds: A review of Pesticide Photochemistry," *Annu. Rev. Entomol.,* 21:61–79 (1976).

Kong, H.-L., et al., "Degradation and total Mineralization of Monohalogenated Biphenyls in Natural Sediment and Mixed Bacterial Culture," *Appl. Environ. Microbiol.,* 46(3):666–672 (Sep., 1983).

Baxter, R. M., et al., "Biochemical and Photochemical Processes in the Degradation of Chlorinated Biphenyls," *Environ. Sci. Technol.,* 18(8):608–610 (1984).

Kearney, P. C., et al., "Oxidative Pretreatment Accelerates TNT Metabolism in Soils," *Chemosphere,* 12:1583–1597 (1983).

PHOTOCHEMICALLY ENHANCED MICROBIAL DEGRADATION OF ENVIRONMENTAL POLLUTANTS

This invention was made with Government support under Grant (or contract) No. NIH ES01963, awarded by DHHS. The Government has certain rights in this invention.

BACKGROUND OF THE INVENTION

1. Field of the Invention

This invention provides for improved methods of biodegradation of environmental pollutants. The invention specifically provides for the simultaneous treatment of the pollutants in a contaminated medium with ultraviolet radiation and lignin-degrading fungi. The fungi are discontinuously contacted with the mass of a contaminated medium. When removed from the mass of contaminated medium, the fungi and adhering contaminated medium are simultaneously exposed to the ultraviolet radiation. The combination of fungal enzymes and ultraviolet radiation enhances the rates of degradation beyond that expected for either of the treatments alone.

2. Information Disclosure

Biodegradation of persistent halogenated organic contaminants is of great interest because of its potential use to cleanup contaminated sites and industrial waste streams on-site (i.e., in situ remediation). Thomas, J. M. and Ward, C. H., In situ biorestoration of organic contaminants in the subsurface, *Environ. Sci. Technol.* 1989. 23:760-766; Daley, P. S., Cleaning up sites with on-site process plants, *Environ. Sci. Technol.* 1989. 23:912-916; Easty, D. B. and Wabers, B. A., Determination of Polychlorinated Biphenyls in Paper Mill Effluents, *Tappi* 61(10):71-74, 1978; and Alexander, M., Biodegradation of chemicals of environmental concern, *Science*, 1981. 211:132-138. Halogenated organic contaminants are known to be highly toxic. The most practical methods of degradation such as incineration are not only expensive but also known to cause secondary pollution problems. Rappe, C., Analysis of polychlorinated dioxins and furans, *Environ. Sci. Technol.* 1984. 18:78A-90A.

Recent studies have shown that lignin-degrading or white rot fungi such as *P. chrysosporium* are able to degrade a variety of highly recalcitrant and toxic compounds. Bumpus, J. A., et al., Oxidation of Persistent Environmental Pollutants Via White Rot Fungus, *Science*, 1985. 228:1434-1436; Aust S. D. Biodegradation of Agrochemicals By White Rot Fungi, In Recent Advances in Microbial Ecology, T. Hattori, Y. Ishda, Y. Maruyama, R. Y. Motira and A. Uchida (eds.), pp 529-533, Japan Scientific Societies Press, Tokyo, Japan; Eaton, D.C. Mineralization of Polychlorinated Biphenyls by *Phanerochaete chrysosporium*: a Ligninolytic Fungus, *Enzyme Microb. Technol.* 7:194-196; Huynh, V. et al., Dechlorination of Chloro-organics by a White Rot Fungus, *Tappi Journal*, 68:98-102, 1985; Mileski, G. J. et al., Biodegradation of pentachlorophenol by the White Rot Fungus Phanerochaete Chrysosporium, *Appl. Environ. Microbiol.* 1988, 54:2885-2889; Hammel, K. E, Kalyanaraman, B., Kirk, T. K., Oxidation of Polycyclic Aromatic Hydrocarbons and Dibenzo(p)-dioxins by Phanerochaete Chrysosporium Lignase, *J. Biol. Chem.* 1986. 261:16948-16952; Bumpus, J. A., Biodegradation of Polycyclic Aromatic Hydrocarbons By Phanerochaete chrysosporium, *Appl. & Environ. Microbiol.*, 55:154-158, 1989; Eaton, T. K. et al., Fungal decoloration of Kraft Bleach Plant Effluents, *Tappi* 63(10):103-106, 1980; and Eaton, D.C. et al., Method Obtains Fungal Reduction of the Color of Extraction-stage Kraft Bleach Effluents, *Tappi Journal*, 65:89-92, 1982.

A general review of the mechanism of microbial degradation of lignin can be found in Kirk, T. K., and Farrell, R. L. Enzymatic "Combustion": The Microbial Degradation of Lignin, *Ann Rev Microbiol* 41:465-505, 1985.

Halogenated hydrocarbons are susceptible to photodegradation by U.V. light. Zabik, M. J. et al., Photochemistry of Bioactive compounds: a Review of Pesticide Photochemistry, *Annu. Rev. Entomol.* 1976. 21:61-79. It has been observed that irradiation by simulated sunlight increased the mineralization rate of 4-chlorobiphenyl in river sediment containing a mixed microbial population (Kong, H.-L., Sayler, G. S., Degradation and Total Mineralization of Monohalogenated Biphenyls in Natural Sediment and Mixed Bacterial Culture, *Appl. Environ. Microbiol.*, 46:666-672 1983) and that microbial actions by a Pseudomonas sp. followed by subsequent irradiation by simulated sunlight degraded the yellow metabolites of 2,4-dichlorobiphenyl (i.e., sequential treatment) Baxter, R. M. and Sutherland, D. A., Biochemical and Photochemical Processes in the Degradation of Chlorinated Biphenyls *Environ. Sci. Technol.* 1984. 18:608-610. In another study, (Kearney P. C., et al. Oxidative Pretreatment accelerates TNT Metabolism in soils, *Chemosphere*, 1983. 12:1583-1597) first treated [$^{14}$C]-2,4,6-trinitrotoluene (TNT) by ultraviolet ozonation and then subjected the products to microbial degradation by *Pseudomonas putida*. Kearney et al. found that pretreatment by UV irradiation helped the metabolic degradation of TNT. However, there has been no successful demonstration of simultaneous application of these two technologies (i.e., use of isolated microbial and ultraviolet treatments) for the degradation of highly recalcitrant compounds.

To date no one has demonstrated that the simultaneous combination of white rot fungi and UV produce a superior means for degrading halogenated organic contaminants.

SUMMARY OF THE INVENTION

This invention provides for a method of degrading halogenated organic compounds in a medium contaminated with said compounds comprising: (a) contacting the medium with a lignin degrading fungus resistant to ultraviolet irradiation; and (b) exposing the medium to ultraviolet light at an intensity sufficient to photochemically decay the hydrocarbons; wherein step a and step b occur simultaneously. The intensity of the ultraviolet light is not such that the fungi are killed. A preferred species of fungi are those selected from the genus Phanerochaete. A preferred species is *P. chrysosporium*.

The method preferably involves the step of treating the medium with an antibiotic prior to contacting with the fungus. Preferred antibiotics are fungicides such as benomyl, triforine, triadimifon, flusilazole and myclobutanil. The method optionally involves the acidification of the medium.

The medium may optionally be treated with an additional carbon source or aeration to enhance the growth rate of the fungi. The fungi are preferably attached to a solid support and more preferably in discontinuous contact with the medium.

More particularly, the method comprises: (a) treating the medium with a fungicide; (b) discontinuously contacting the medium with a strain of P. chrysosporium, resistant to ultraviolet irradiation; (c) adding a carbon source to the medium in an amount sufficient to maximize the growth of the P. chrysosporium; (d) exposing the P. chrysosporium and medium to ultraviolet light at an intensity sufficient to degrade the compounds; and, (e) incubating the medium to permit degradation of the compounds by the P. chrysosporium; wherein steps d and e occur simultaneously.

This invention further provides for a system for degrading halogenated organic compounds in a medium, said system comprising: (a) a housing having an access to the outside and defining a space wherein a portion of the space is suitable for containing the medium; (b) a solid surface support positioned within the space and having a surface permitting hyphal attachment by lignin degrading fungi; (c) a means for contacting the medium with the lignin degrading fungus; and, (d) a source of ultraviolet light able to produce sufficient energy to degrade the halogenated organic compounds and arranged to illuminate the support and a portion of the space. The system preferably comprises a plurality of rotatable discs as the solid surface support. Even more preferred is a system where the means for contacting the medium with the fungus comprises an rotatable axle to which the solid surface support is attached.

This invention also provides a strain of P. chrysosporium derived from the strain deposited with the ATCC of Rockville, Md. having the Accession No. 74046, deposited on Apr. 10, 1991. This strain is particularly well-suited for use in the above described method and system.

DEFINITIONS

By "degrading halogenated organic compounds", it is meant that the halogenated organic compounds are reduced to non-toxic components. Typically this is mineralization of the hydrocarbons to carbon dioxide and water.

By "fungus resistant to ultraviolet light" it is meant that rate of hyphal elongation under UV irradiation of 7000 $\mu$watts/cm$^2$ at either 300 or 254 nm is at least 50% of the rate for the same strain under optimum growing conditions.

By "halogenated organic compounds" it is meant halogen substituted hydrocarbons inclusive of noncyclical compounds, cyclical compounds having aromatic or nonaromatic rings, and heterosubstituted organic compounds having one or more carbon atoms replaced by a sulfur, nitrogen or other noncarbon atoms. The halogen atoms include chorine, iodine, bromine and fluorine.

By "ultraviolet light at an intensity sufficient to photochemically decay the organic compounds," it is meant that the light can be absorbed as a photon by the compound molecules which results in the disappearance of the that molecule. Photochemical decay can involve a series of events. The first step usually involves the formation of a free radical, intramolecular rearrangements or other excited molecules which in turn react in secondary processes to from new products.

By "oxygenating the medium" it is meant that the medium is treated with oxygen or air to offset an anaerobic environment. This can be achieved by bubbling air through the medium or by physically agitating the medium.

DETAILED DESCRIPTION

Figure 1:
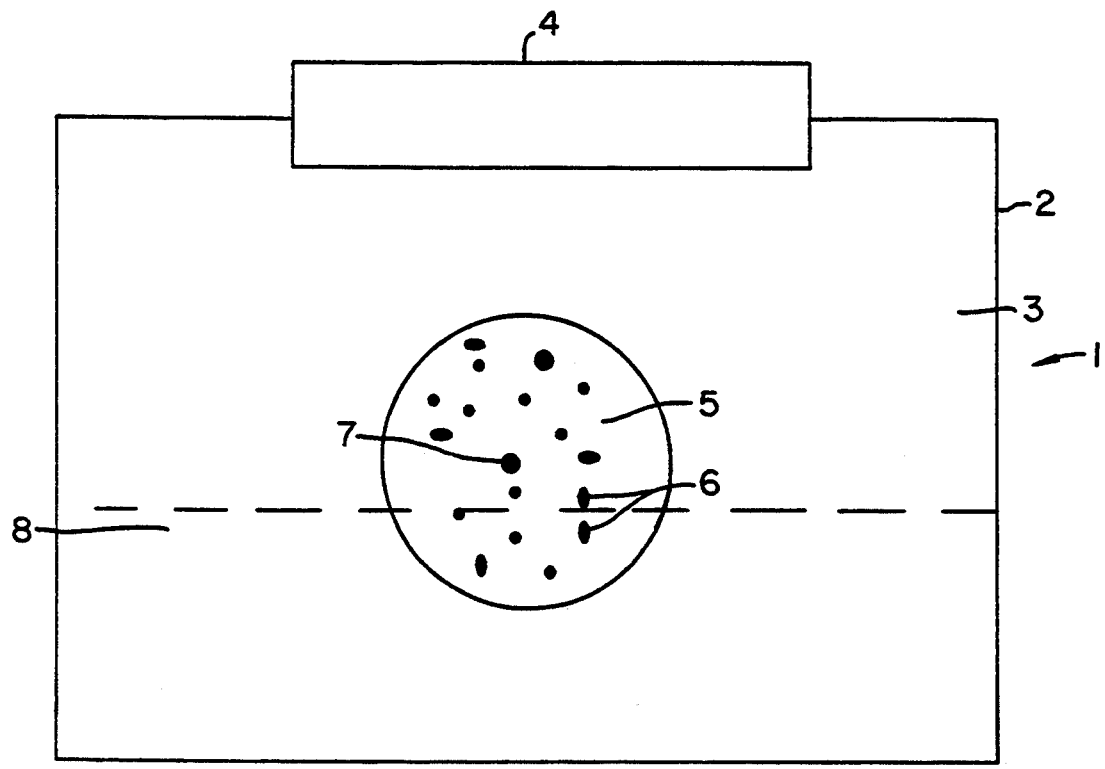
FIG. 1 is a schematic representation of the system and its component parts.
Figure 2:
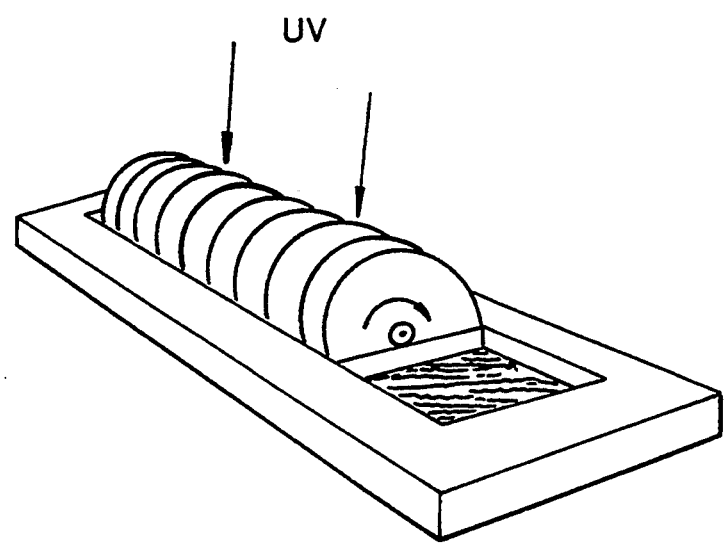
FIG. 2 is a top view of the system revealing a plurality of disc supports in an open housing.

The invention disclosed herein is useful for degrading toxic pollutants contaminating the environment. It is particularly suited for degrading halogenated aromatic hydrocarbons.

Halogenated organic compounds include pesticides such as aldrin, endtin, endosulfan, DDT (dichlorodiphenyl-trichloroethane), dieldrin, diflubenzuron, heptachlor, 3,4,3',4'-tetrachlorobiphenyl (3,4,3',4'-TCB), and toxaphene (polychlorocamphenes) and herbicides such as dioxin derivatives (e.g., 2,3,7,8-tetrachlorodibenzo-p-dioxin), chloramben, bromoxynil, profluralin, sesone and 2,4-DEP (2,4-dichlorophenoxy)ethyl phosphite). Many of the halogenated (especially chlorinated) organic compounds have been banned for use as pesticides and herbicides because of their acute toxicity, their tendency to accumulate in the tissues of desirable organisms and their inability to degrade naturally in the environment.

Halogenated organic compounds also includes polychlorinated biphenyl compounds commonly known as PCB. PCB originates from biphenyl, terphenyls, higher polyphenyls, or mixtures of these compounds which are chlorinated to give a wide range of products that are chemically and thermally stable. Commercial preparation of PCB's involves the direct chlorination of biphenyl to yield mixture of isomers that have quite different physical properties. Commercial applications included use in transformers, capacitors, hydraulic and heat transfer liquids, waterproofing materials, plasticizers, and other uses.

PCB's are well known as toxic contaminants in our environment. Domestic production of polychlorinated biphenyls was stopped in 1977 because of the tendency of these products to accumulate and persist in the environment. They are highly stable and are resistant to biological degradation. The ultimate disposal of PCB's until this invention was the use of incineration and heats in excess of 1100° C. This typically requires special incinerators that prevent the PCB's from vaporizing before they are converted to their constituent form of carbon dioxide, water and hydrogen chloride.

The majority of PCB's in the environment are mixtures of isomers of trichlorobiphenyl, tetrachlorobiphenyl, pentachlorobiphenyl, and small amounts of dichlorobiphenyl and hexachlorobiphenyl.

The system and method described herein degrades halogenated organic compounds from both aqueous and non-aqueous environments. The combination of fungi and UV radiation can be useful for removing these toxins from contaminated medium such as water, sludge, mud, soil, and industrial waste. By following, the guidelines presented below, those of skill will readily recognize that routine engineering modifications may be needed to optimize the exposure of the contaminated medium to both the fungi and UV irradiation.

UV irradiation of halogenated organic compounds in close proximity to the fungi can be achieved by the use of commercially available UV lamps. The wavelength of UV radiation should be within about 254 nanometers to about 300 nanometers. Different chemical contaminants will photodecay more effectively at different wavelengths. Optimum wavelengths can be selected for the optimum degradation of any particular halogenated organic compounds being degraded. The intensity of radiation should range from about 4000 microwatts per square centimeter to about 8000 microwatts per square centimeter, the intensity and time duration of the radiation should be balanced to optimize contaminant degradation while not unduly inhibiting the growth rate of the fungi.

Sources of UV lamps are widely known. For example, Model 3-3100 from Fotodyne, Inc. 16700 W. Victor Rd.; New Berlin, Wis. 53151.

Because different contaminants photodecay more strongly at specific UV wavelengths, some knowledge of the effects of UV irradiation upon the contaminants is helpful. This can be achieved empirically by varying the wavelength of UV while monitoring the rates of degradation. Alternatively, optimum wavelengths can be selected by having prior knowledge of the contaminants present in the medium being treated and consulting publicly available sources for information regarding the photoreactivity of those contaminants. See for example, Zabik and Leavitt, *Annual Review of Entomology*, 21:61–79, 1976.

Lignin-degrading fungi, particularly appropriate for use in this invention, are generally known as white rot fungi. The white rot fungi are a generic class of basidiomycetes with the ability to degrade lignin. Lignin is a naturally-occurring complex aromatic hydrocarbon polymer made by plant cells. It has been described as the most abundant renewable aromatic material on earth. It typically comprises a complex polymer of coumaryl alcohol, coniferyl alcohol, and sinapyl alcohol. Most lignin is found within the cell walls of plants, where it is intimately interdispersed with the hemicelluloses forming the matrix that surrounds the orderly cellulose microfibrils. In wood, lignin in high concentration is the glue that binds the contiguous cells forming the middle lamella.

The white rot fungi degrade lignin more rapidly and extensively than any other of the studied microbial groups. Like the brown rot fungi, they enter the lumen of wood cells where they secrete enzymes that degrade lignin and other wood components. The white rot fungi, unlike the brown rot fungi, selectively degrade lignin along with the hemicelluloses. The process of degradation is known as mineralization. The mineralization process appears to occur at some distance from the fungal hyphae which indicates that the fungi are producing enzymes and secreting them into the environment.

Table 1 provides a list of commonly found white rot fungi that would be of use in this invention. Because the method contemplates simultaneous exposure of the contaminated medium to fungi and UV irradiation, it is preferred that the fungi be able to grow vigorously under the conditions provided. The fungi is preferably preselected for tolerance of UV radiation. To achieve resistance to UV irradiation, it is necessary to selectively grow the fungi under UV irradiation with incrementally increasing exposure as to both time and intensity of UV radiation. Exposures of unselected strains should begin at UV levels which are nonlethal yet retard growth by 50%.

TABLE 1

| Lignin degrading fungi |
| --- |
| *Polyporus versicolor* |
| *Armillaria mellea* |
| *Armillaria mellea* (Vahl. ex Fr.) Quel |
| *Phlebia brevispora* |
| *Ganoderma biownii* |
| *Phellinus gilvus* |
| *Lentinus betulia* |
| *Trametes versicolor* |
| *Ganoderma lucidum* |
| *Trametes hirsutam* |
| *Inonotus cuticularis* |
| *Ganoderma lucidum* |
| *Armellaria mellea* |
| *Chrysonilia sitophila* |
| *Phanerochaete chrysosporium* |
| *Coriolus versicola* (L. ex. Fr.) Quel |

For example, fungi can be selected to grow at 254 nanometers, exposure for one hour at 2000 microwatts per square centimeter per day, and this can be increased to 6000–7000 microwatts per square centimeter of radiation at 254 nanometers for a minimum of two hours exposure per day in increments varying according to the three parameters of time, intensity and wavelength until a suitable strain is selected. A useful method for screening fungi for UV resistance, involves placing a piece of hypha in the center of 3% malt extract agar plate and incubate the plate in the dark at 25° C. to allow for linear elongation of the hypha. UV irradiation can be done through a polystyrene petri dish cover or polyvinyldine cover sheet. By adjusting the carbon and nutrient supplements and by judicious selection of the UV parameters, one can obtain strains of white rot fungi which can degrade chlorinated aromatic hydrocarbons in the presence of UV radiation.

After sufficient UV resistance has been demonstrated in the asexual form, it is useful to transfer the selected fungi to conditions which permit sexual reproduction. Demonstrating that the UV resistance is conferred to the subsequent generation assures that the resistance is a result of a genetic change rather than merely a temporary response to environmental stimuli.

A particularly good species for obtaining a UV resistant white rot fungi is *P. chrysosporium*. A suitable strain was deposited in accordance with Budapest Treaty with the American Type Culture Collection [ATCC] located at 12301 Parklawn Dr., Rockville, Md., USA 20852 on Apr. 10, 1991 and given accession number ATCC 74046.

For commercial applications of this invention, it is preferred that the contaminated medium harbor a minimum number of competing organisms, especially fungi that might compete with the white rot fungi for nutrients. To eliminate competing microorganisms, the medium can be pretreated with antibiotics which include both bactericides and fungicides. By pretreating the medium with an antibiotic, it is meant that the medium has been treated to substantially inhibit the growth of competing microorganisms. It is not necessary to totally eliminate all microorganisms. Preferred fungicides include benomyl (100 ppm), triforine (25 ppm), triademefon (2 ppm), flusilazole (2 ppm) and myclobutanil (1 ppm).

The obtention of a white rot fungi that is resistant to at least one antibiotic is within the skill in the art. The basic procedure involves the exposure of actively growing hyphae to increasing amounts of antibiotic. The use of sublethal doses of antibiotic will inevitably retard growth of the initial strains. By comparison of the growth rates of the fungi exposed to antibiotic to that of control fungi under optimal growing conditions it is possible to monitor the ability of strains to resist the effects of an antibiotic.

Fungal degradation of the toxic compounds described herein is achieved by a combination of UV radiation in an aerobic or oxygen-rich environment. Depending upon the contaminated medium, the UV radiation may be unable to penetrate the surface. It is also possible that the contaminated medium might comprise an anaerobic environment.

To ensure that the above conditions are met, it is useful to contact the fungi and the contaminated medium in a discontinuous operational mode. By discontinuous, it is meant that the exposure of the fungi in contaminated medium is such that the fungi spends a portion of its life cycle in contact with the contaminated medium and a portion of its time away from the mass contaminated medium wherein it is exposed to an oxygen-rich atmosphere and to the UV radiation needed to maximize degradation of the contaminants.

The method described above preferably takes place in a multi-component system designed to enhance contaminant degradation by controlling fungal growth, UV light and contact of pollutants with the fungi. More specifically, systems (1) suitable for use in this invention would comprise a housing (2) enclosing a space (3) wherein contaminant degradation takes place. The housing (2) could be either a closed housing, being a full sided enclosure with closable openings or an open housing with constant access to the outside. The housing (2) comprises, contains, or is attached to an ultraviolet light source (4) as described above. The light source is arranged so that it illuminates the space. The housing would further contain mycelial support surfaces (5) which can provide support for fungal mycelial mats (6). These solid support surfaces (5) are attached to a means (7) for discontinuous contacting of the surfaces with the medium (8) contained within a portion of space (3) within the housing (2). Means (7), can comprise an axle or other linkage connected to a motor, not shown. The combination of motor and means (7) mechanically change the relative position of the surface (5) to repeatedly contact and remove fungi (6) from the contaminated medium (8). Alternatively, the surfaces could be stationary and the contaminated medium can be agitated to contact the surfaces such as in the forms of a spray. The systems (1) are optionally climate controllable to provide an optimum temperature for fungal growth.

The systems optionally will provide an intake and outlet for atmospheric exchange. Either normal air or select atmospheric environments (oxygen enriched) may be used to optimize fungal growth. The solid surface support (5) for the fungi can either be single or a multiple number of supports. The support must permit adhesion of the fungal hypha. Supports may be made of lucite, frosted glass, polystyrene, stainless steel, ceramics or any other corrosion-free plastics or metal materials. A porous, toughened surface is useful to facilitate hyphal attachment.

The supports can shaped as prongs which can be lowered into and raised from the contaminated medium. In an alternative embodiment, the surface supports may be in the form of rotatable discs which are partly submerged into the contaminated medium. As the discs rotate, the mycelial mats are discontinuously placed in contact with the contaminated medium.

The UV lamps can be placed outside or within the space (3) and arranged to irradiate the fungi growing on the support surfaces. The lamps should be arranged to ensure that illumination is relatively uniform. A timer is useful to provide a controllable period of UV irradiation.

One system design uses available rotating biological contactors such as the MyCor Reactor produced by North Carolina State University and Forest Product Lab, Madison, Wis. The rotating biological contactors, also known as RBC's, are comprised of a series of disks made of a suitable material for mycelial adhesion which are rotated so that a portion of the disk at any one time is below the surface of the contaminated medium, and the remaining portion of the disk is above the medium surface, exposed to the atmosphere and UV radiation.

The disks can be of any size. The rate of rotation is typically 1–2 rotations per minute.

The exposure of the disks to UV light should be about equal and should be within the ranges given above, namely anywhere from one-half hour to four hours per day and at a wavelength from 254 to 300 nanometers with an intensity optimally of 500 to 8,000 microwatts per square centimeter. The exposure to UV of the mycelial mat to UV radiation need not be continuous for the entire time duration. The length of exposure will vary with the fungi's ability to tolerate the light. Control of the atmosphere in the biological contactor is not always necessary. Normal atmospheric conditions are acceptable. The temperature should be anywhere from 23° to 45° C.

The growth rate of mycelium is directly proportional to the rate of degradation of the pollutants. To enhance growth rates, it may be useful to provide supplemental nutrients to the contaminated medium. Such supplements may be a carbon source such as glucose, fructose, sucrose or other hexose or pentose sugars; nitrogen sources such as nitrogen sulfate; and additives providing trace elements such as yeast and malt extracts and bactopeptone. The degrading ability of Chrysosporium sps. is considered to be largely due to ligninase produced in nitrogen-deficient culture. However, in the combination test with the fungus and ultraviolet at 300 nm, we found that the degradation of 3,4,3',4'-TCB (trichlorobiphenyl) was enhanced even in nitrogen-rich culture which was prepared by the addition of 1 mg $NH_4NO_3$ to a liter of medium.

The ratio of mycelium mass to contaminated medium will directly affect the rate of contaminant degradation. It is not possible to provide precise guidelines as to this ratio. The optimum ratio will vary with the fungi, the contaminant being degraded, environmental conditions, the presence of competing microorganisms, the medium being treated whether fluid or solid, the quality and quantity of UV radiation. The selection of fungi strains which overproduce the enzymes used to degrade contaminated medium will enhance the efficiency of the system and lower the ratio of mycelium mass to contaminated medium needed to achieve commercially acceptable rates of contaminant degradation. Less than optimum growth conditions will increase the ratio. As a rough guide, one should have approximately 10 gms of mycelium to 0.1 gms of contaminated medium to achieve commercially useful degradation rates.

The following examples are for illustrative purposes. They are not meant to be a limitation of the invention disclosed herein. Those of skill will readily recognize variations of non-critical parameters can be used to achieve substantially the same results.

EXAMPLES

1. An ultraviolet and fungicide resistant strain of *Phanerochaete chrysosporium*

To obtain an ultraviolet resistant strain of *P. chrysosporium*, the prospective isolates are initially screened for their native sensitivity to ultraviolet radiation. The isolates are cultivated on malt agar as described in Table 2 at 30° C. under dark conditions. The cultures are first exposed to irradiation at 300 nm (3000 $\mu$watts/cm$^2$) for two hours per day. The sensitivity to ultraviolet radiation was measured against the fungal elongation of non-irradiated cultures. The growth rates for the unselected strains ranged from 0% (death) to 80% of the non-irradiated cultures. The naturally resistant strains can be made further resistant by repeated selection until the growth rates under 7000 $\mu$watts/cm$^2$ approximate non-irradiated fungi.

Following selection of U.V. resistant strains of *P. chrysosporium*, the strains are exposed to the fungicide, benomyl at 100 $\mu$g/ml (100 ppm) and grown at 25° C. The benomyl resistant colonies grown are then transferred to nitrogen-deficient broth and irradiated with ultraviolet at 300 nm at 3,000 $\mu$W/cm$^2$ for 2 hours a day for 4 weeks.

To ensure that resistance is genetically based the *P. chrysosporium* isolates are allowed to form conidia (without UV irradiation) and resistance is determined. No sporulation occurs under the harsh conditions of U.V. irradiation and fungicide. To obtain conidia, a piece of hyphae was transferred to YH agar slant without benomyl. Following these procedures, a final strain, doubly resistant to ultraviolet and benomyl was obtained, named as BU-1 and used in the test described below.

TABLE 2

| YM agar | |
|---|---|
| Yeast extract (Difco*) | 3.0 g |
| Malt extract (Difco) | 3.0 g |
| Bactopeptone (Difco) | 5.0 g |
| Dextrose (any source) | 10.0 g |
| Agar noble (Difco) | 20.0 g |
| Distilled water | 1 liter |
| PH will become 6.2 ± 0.2 | |

*Difco Laboratories, Detroit Michigan

2. The synergy of UV light and *P. chrysosporium*

Figure 3:
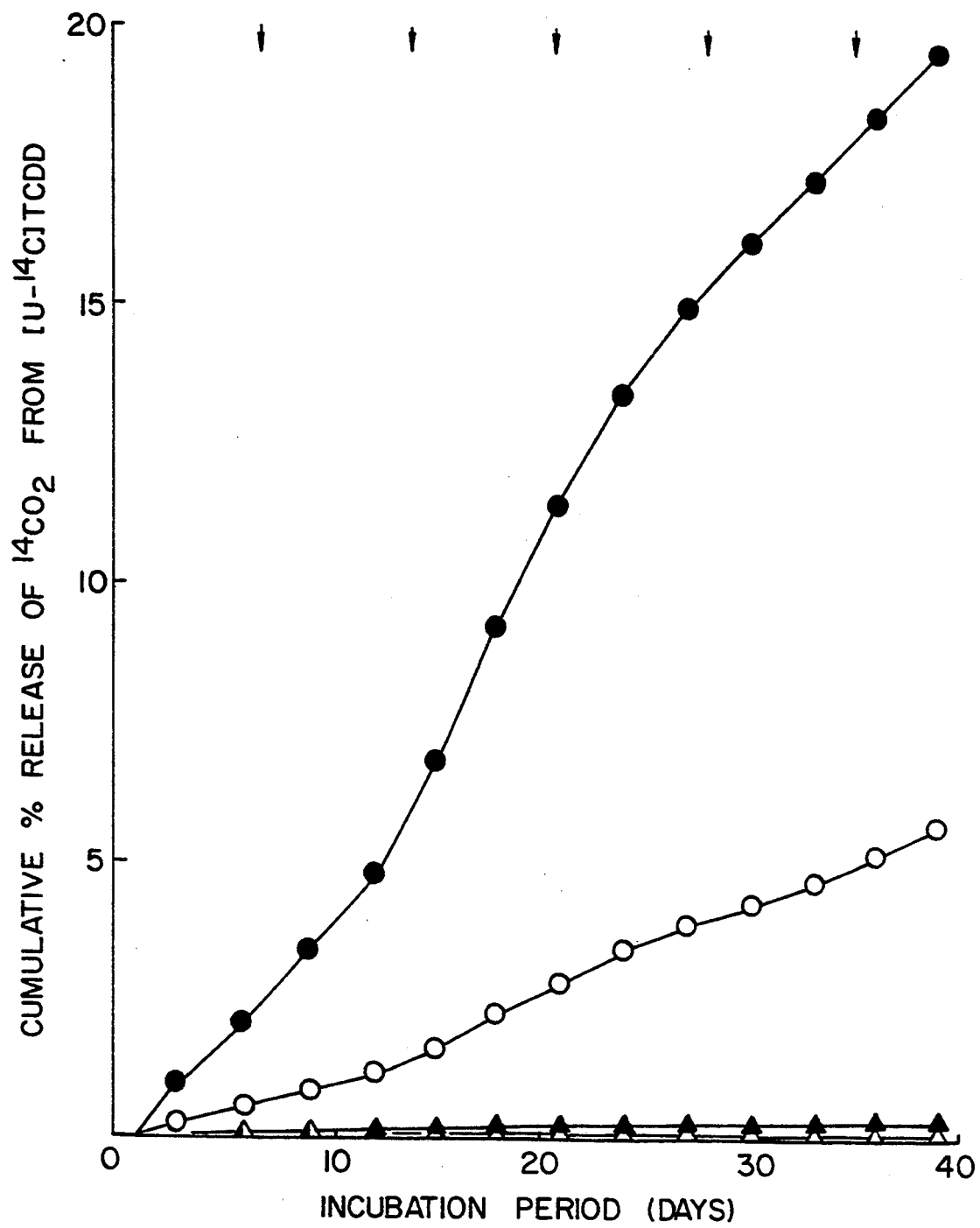
FIG. 3—Mineralization of [U-$^{14}$C]TCDD to 14CO$_2$ by the simultaneous actions of P. chrysosporium BU-1 and 300-nm UV irradiation (●) as compared to solo treatment by UV irradiation only (○), fungus only (▲), and blank [no fungus and no UV, (△). Glucose (10 mg) was added every 7 days (shown as arrows). The values are averages of triplicate tests and expressed as percents of initial $^{14}$C. The standard deviation was 2.1% in the combination system, 1.3% in the UV-only system, 0.11% in the fungus-only system, and 0.04% in the blank.

In an initial study, it was established that simultaneous application of UV-irradiation (at 300nm, 2 hours a day) and BU-1 in a nitrogen-deficient medium caused a much more accelerated rate of mineralization of dioxin, [U-$^{14}$C] TCDD (2,3,7,8-tetrachlorodibenzo-p-dioxin), than achieved by either of UV-irradiation or BU-1 alone (FIG. 3). The study was conducted in a small reactor containing 1000 half filled with a nitrogen deficient medium comprising the components listed in Table 3.

Under both UV irradiation and in the presence of *P. chrysosporium*, the mineralization of dioxin continued constantly until the end of the experiment, and the amount of [U-$^{14}$CO$_2$] produced reached 20% of the initial radioactivity after 40 days incubation. In parallel experiments TCDD was treated in the same medium by irradiation only resulting in a mineralization level of 5.8%. The corresponding figures were 0.27% in the test with the fungus alone and 0.19% without irradiation or inoculation of fungus.

Figure 4:
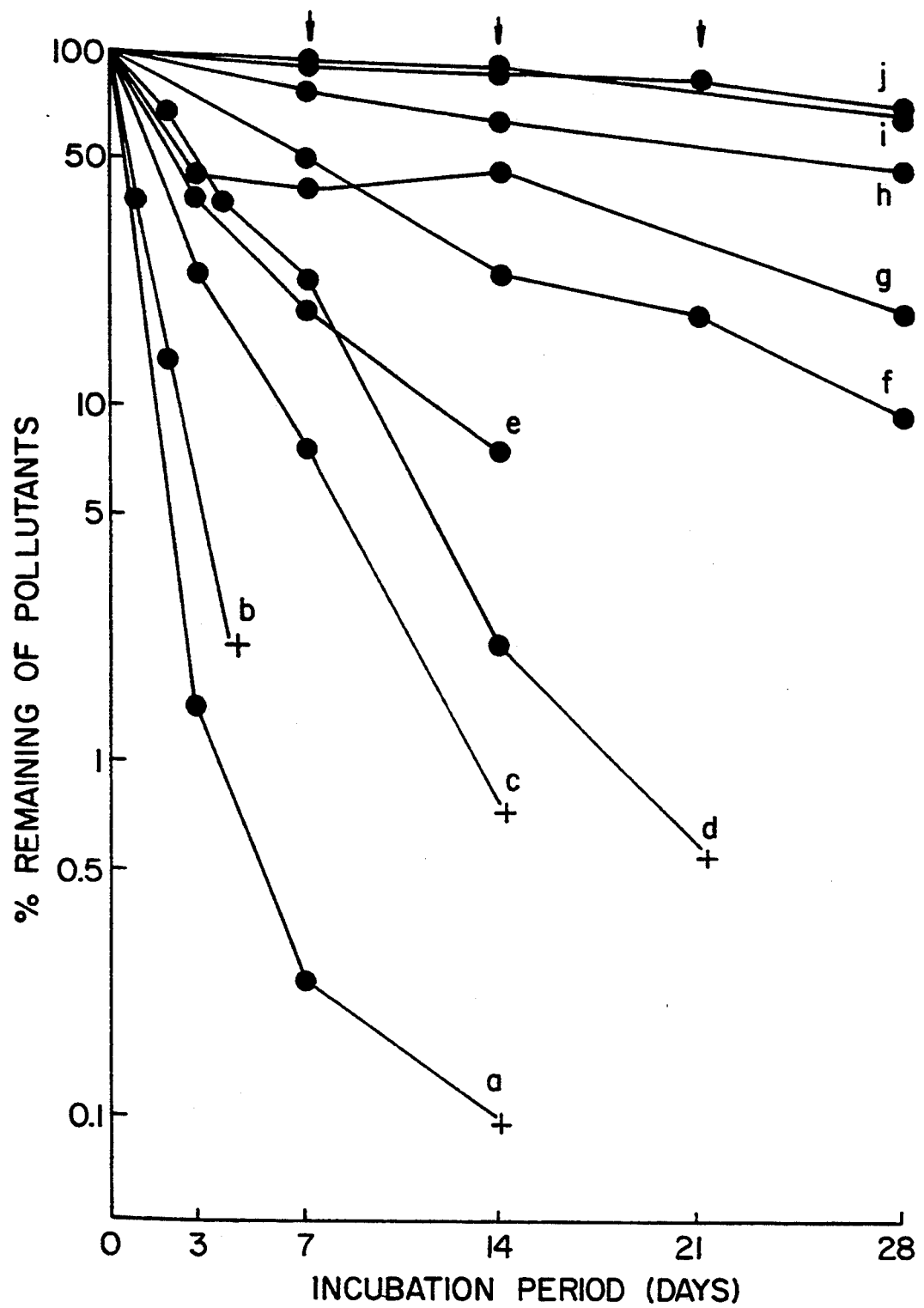
FIG. 4—Disappearance of persistent pollutants during the simultaneous treatment using P. chrysosporium BU-1 and UV (either 254 or 300 nm) irradiation. (a) DDT in combination with 254-nm UV, (b) TCDD with 300-nm UV, (c) heptachlor with 254-nm UV, (d) TCB with 300-nm UV, (e) heptachlor with 300-nm UV, (h) toxaphene with 254-nm UV, (i) toxaphene with 300-nm UV, (j) dieldrin with 300-nm UV. The values are duplicate flask averages of two independent tests and are expressed as percents of the initial amount (1 mg) of pollutants. Duplicate tests varied less than ±10%. The sign + indicates that the residue level reached less than the detection limits for each compound under the analytical technique used. Glucose (10 mg) was added every 7 days (shown as arrows).

3. The ability of UV light and *P. chrysosporium* to effectively degrade a wide range of toxic environmental pollutants In a second series of experiments, the rates of disappearance of DDT, dieldrin, heptachlor, 3,4,3',4'-tetrachlorobiphenyl (3,4,3',4'-TCB), toxaphene and 2,3,'7,8-tetrachlorodibenzo-p-dioxin (2,3,7,8-TCDD) were studied. These experiments used a petri dish method. The petri dish method comprises the nitrogen deficient media provided in Table 3. The assay is conducted a polycarbonate petri dish 10 cm diameter ×1.5 cm depth, with 20 ml medium per petri dish. In 1/10 scale experiments 3.5 cm diameter petri dishes with 2 ml medium/dish were used. The disappearance of the original compounds were monitored by gas chromatography. Reaction products were extracted with a 30 ml mixture of hexane and 40% $CaCl_2$ (2:1), and centrifuged at 700 $\times$ g. The upper layer was collected and a 1 ul portion was injected to gas-liquid chromatographic system equipped with a 10% OV-101 chromosorb AW-DMCS 80/100 mesh column and an electron-capture detector. The column temperature was 200° to 225° C. The results are provided in (FIG. 4).

TABLE 3

| Nitrogen deficient medium | |
| --- | --- |
| N-deficient medium | |
| D-glucose | 10.0 g |
| $NH_4NO_3$ | 0.05 g |
| L-asparagrine $H_2O$ | 0.1 g |
| $KH_2PO_4$ | 0.2 g |
| $MgSO_4$ anhydrous | 0.025 g |
| $CaCl_2 2H_2O$ | 0.01 g |
| 2,2-dimethyl succinate buffer (DMSB) (0.731 g DMSB/100 ml $H_2O$ add NaOH to pH 4.5) | 100 ml |
| Mineral salt* | 1 ml |
| Vitamin solution* | 0.1 ml |

*Zeikus, J. G. & Wolfe, R. S. (1973) J. Bacteriol. 113:461–467

The combined treatments of the fungus and UV, either at 254 nm or 300 nm, resulted in more that 97% of initial amount of DDT, 2,3,7,8-TCDD, heptachlor and 3,4,3',4'-TCB being metabolized in 3 weeks of incubation. The combined treatments with ultraviolet at 254 nm resulted in 92% of dieldrin and 52% of toxaphene being degraded in 4 weeks. Except for the combination with ultraviolet at 300 nm for DDT, disappearance curves on the logarithmic scale for most of the compounds were close to the straight lines indicating first order kinetics.

In view of past criticism in this field, that microbial degradation technologies tend to have a problem eliminating the last few percents of the toxics, a conscious effort was made to prove that this system could continue to degrade the contaminants to the level where one could no longer find any residues by available analytical techniques. In the data shown in FIG. 4, we could show in 4 of the fastest degrading systems that the residue level reached to the detection limits for each compound within the study period. These four systems are a–d and are marked with a (+). A study by petri dish method using [U-$^{14}$C] TCDD showed that 8.8 ng/ml of initial concentration decreases to 31±10 pg/ml after 7 days of incubation and to less than detection limit of TCDD (10 ppt) after 14 days. (FIG. 5) FIG. 5 also demonstrates the enhancement of degradation by the addition of a carbon source.

Using DDT, dieldrin, toxaphene, 3,4,3',4'-TCB and 2,3,7,8-TCDD, the synergistic and antagonistic effects of combination on the rates of degradation were examined (Table 4). In the case of degradation of 3,4,3',4'-TCB and 2,3,7,8-TCDD, the combination of these two technologies always produces synergistic actions. In the degradation of DDT and toxaphene, the action of 300 nm ultraviolet was not synergistic to microbial actions, though 254 nm irradiation always caused higher rates of degradation than those obtained by the action of the fungus alone.

TABLE 4

Stimulatory and non-stimulative effects of the combined actions of *P. chrysosporium* and UV irradiation on degradation of persistent pollutants*

| Pollutants | Incubation period (days) | UV irradiation (in the presence of fungus) | | |
| --- | --- | --- | --- | --- |
| | | none | UV254 % (remaining) | UV300 |
| DDT | 7 | 24 ± 2 | 0.2 ± 0.1 | 42 ± 6 |
| dieldrin | 7 | 99 ± 2± | 41 ± 2 | 67 ± 4 |
| 3,4,3',4'-TCB | 7 | 73 ± 7 | 47 ± 10 | 24 ± 8 |
| 2,3,7,8-TCDD | 4 | 44 ± 19 | 41 ± 14 | 3 ± 3 |

*The effects of ultraviolet irradiation only could not be evaluated by the petri-dish method because of the volatilization.

4. Heat stable photosensitizers aid in the degradation of the test pollutants

Figure 5:
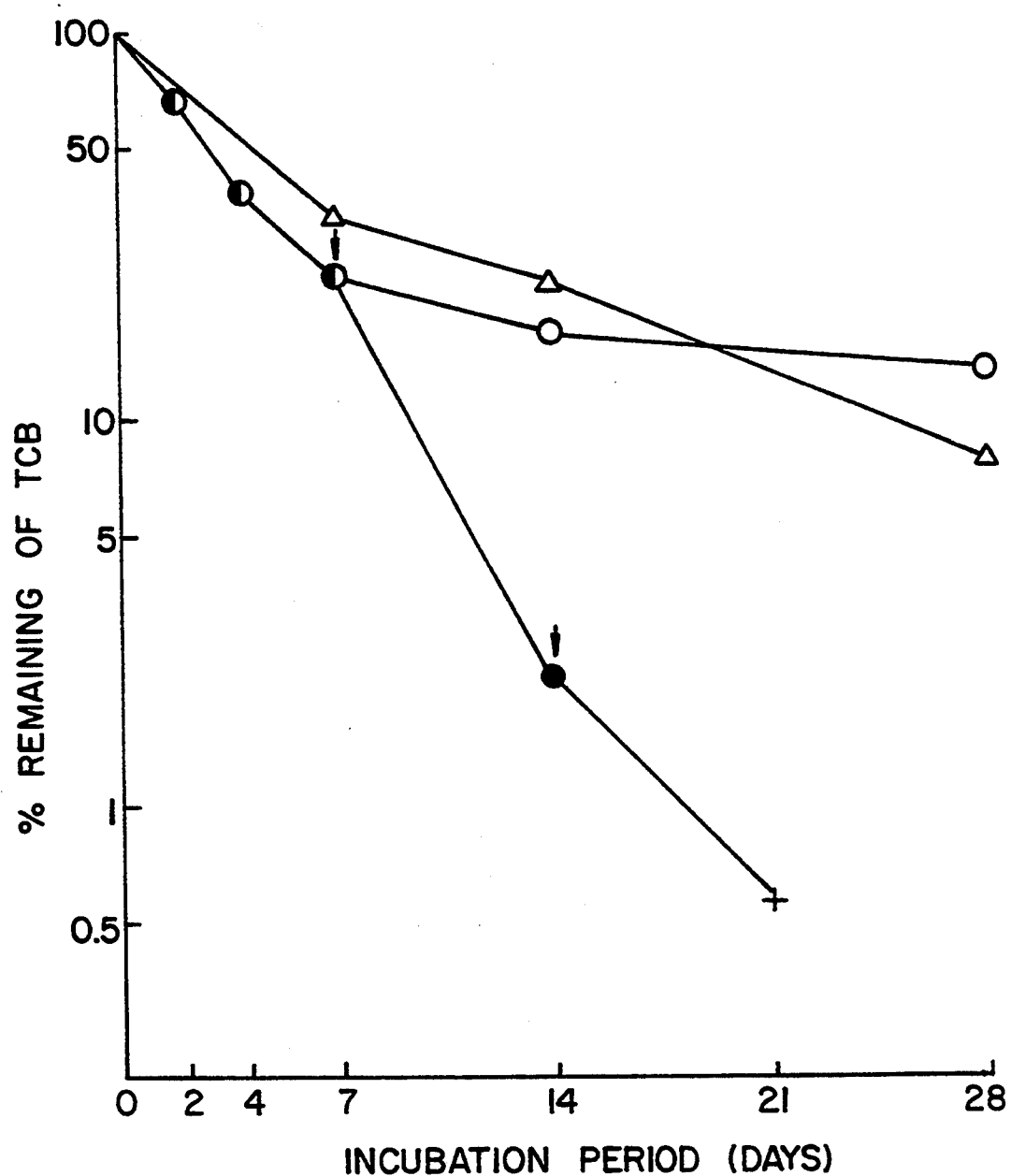
FIG. 5—The rejuvenating effect of glucose on the combined degradative actions of UV (300 nm) and P. chrysosporium BU-1 on 3,4,3',4'-tetrachlorobiphenyl (one of PCB components). Glucose was added (•••) to one of the reactors at points indicated by arrows. The controls used for this experiment are: those that received no glucose (•••) and the same with dead fungi (▲—▲) autoclaved). Both controls received the same level of UV exposure as the rejuvenated (i.e. glucose added) reactor.
Figure 6:
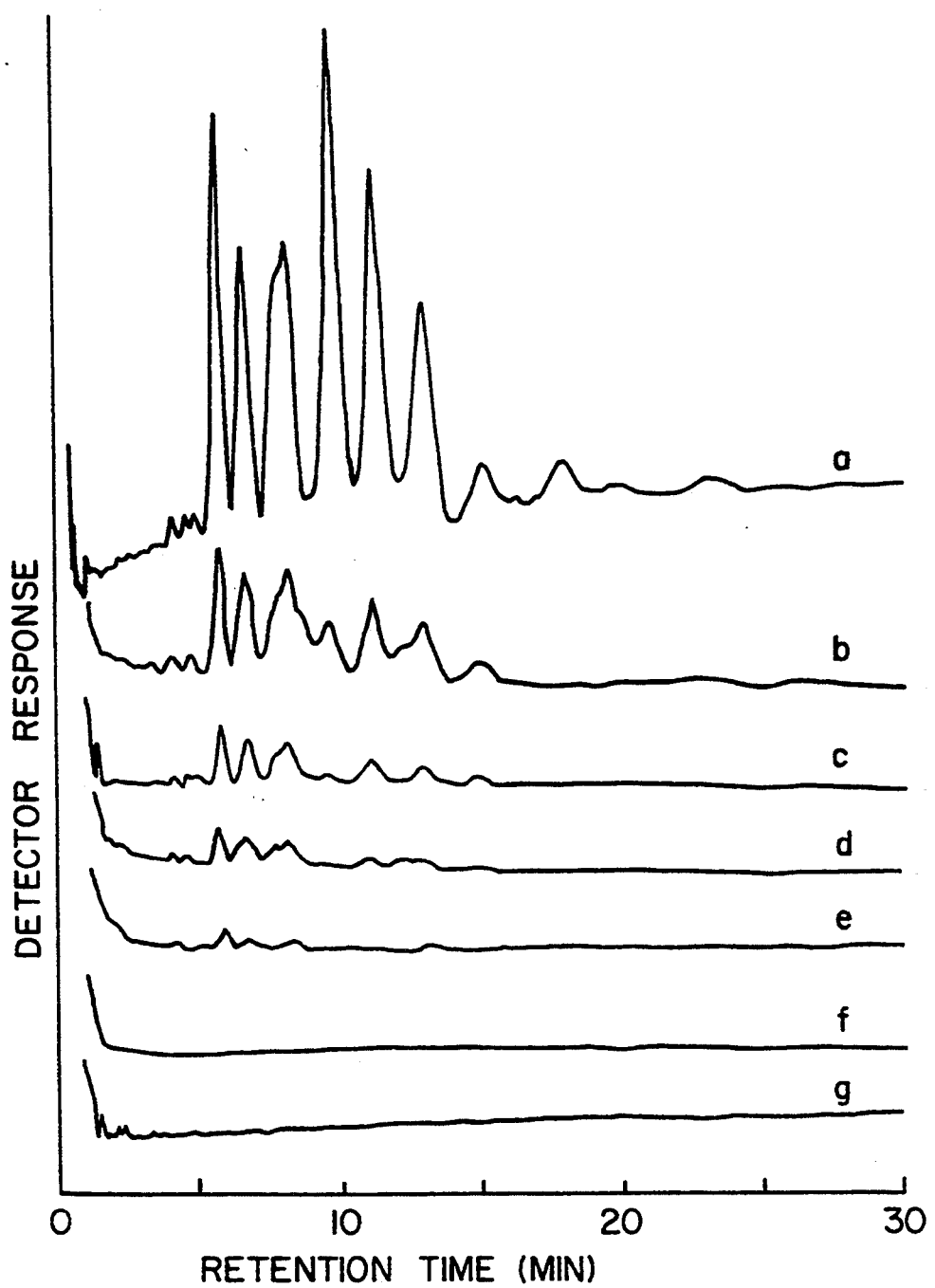
FIG. 6—Degradation of Aroclor 1254 by the combined action of P. chrysosporium BU-1 and UV irradiation (300 nm). (a) The original extract of Aroclor from the medium at 1 day. (b—e) Aroclor 1254 residues after 3, 7, 14, and 28 days, respectively, of incubation with UV at 300 nm. (f) The blank treated for 28 days (culture without the addition of Aroclor 1254) (g) Same as (e) except that the UV source was 254 nm (after 28 days). Note that no stable products were found to accumulate by these treatments, indicating that this technology is applicable to a wide range of PCB congeners (even very highly chlorinated biphenyls), related chemicals, and reaction products.

To test whether the degradation of the toxic pollutants was due to enzyme proteins such as ligninase, the ability of heat sterilized spent culture medium was tested for the ability to degrade a polychlorobiphenyl, Aroclor 1254 manufactured by Monsanto. *P. chrysosporium* was cultured with the Aroclor 1254 (0.1 mg/ml) in the nitrogen deficient medium provided in Table 3. The medium was assayed at 0 min and 3, 7, 14 and 28 days of incubation at 7000$\mu$watts/cm$^2$ at 300 nm or 800$\mu$watts/cm$^2$ at 254 nm, both for 2 hr/day. As can be seen in FIG. 5, the autoclaved culture containing dead fungal mycelia and spent medium enhanced the degradative action of Aroclor 1254 by ultraviolet at both 300 and 254 nm. These findings suggest that for some pollutants, the ligninase may not be the major means responsible for degradation and that there are some microbially produced heat-stable photosensitizers which assist photodegradation of certain chemicals.

5. An example of degradation of Aroclor 1254 by using combined actions of UV-irradiation, *P. chrysosporium* BU-1 and a rotating biological contactor (RBC) system The RBC system used was a 3 liter size plastic box (1L medium size) with 5 discs (10 cm diameter) made of polycarbonate clear plastics. The surface of the discs were scratched by filing to facilitate attaching of fungal mycelia. BU-1 was introduced to 1 liter of N-deficient medium, which is described in Table 3, and allowed to grow for 7 days with 2 hr/day irradiation of UV at 300 nm. The discs were rotated at 2 rpm using a small electric motor. Approximately 40% of the surface area of each disc was submerged into the medium. The fungus grew well to form "mylelial mats" on both sides of each disc. At the end of this preincubation period 100 mg of Aroclor 1254 (Analab Inc., lot K040) were added to the medium with enough volume of acetone-ethanol to dissolve this quantity of Aroclor 1254. The change in Aroclor concentration in the medium was monitored from time to time by taking an aliquot of the medium extracted into hexane of analyzing on gas chromatography as before. After 23 days when almost all of the initially added Aroclor has disappeared, a second 100 mg of Aroclor 1254 was added to the system and monitoring was continued up to 43. The results show in the accompanying figure clearly demonstrate that this system is capable of degradating Aroclor 1254. Within this time span, all of the initial 100 mg quantity was degraded, and furthermore, approximately 99% of the second batch of 100 mg added were degraded.

What is claimed is:

1. A method of degrading a halogenated organic compound in a medium contaminated with said compound, wherein said compound is selected from the group consisting of endosulfan, dichlorodiphenyltrichlorethane, dieldrin, dioxin, heptachlor, 3,4,3',4'-tetrachlorobiphenyl, and toxaphene, and wherein said medium is capable of supporting growth of *Phenerochaete chrysosporium*, comprising the steps:
   (a) contacting the medium with *Phanerochaete chrysosporium* strain ATCC 74046 or mutants thereof possessing all of the identifying characteristics of the parent strain under conditions such that the *Phanerochaete chrysosporium* can degrade said compound; and
   (b) exposing the medium to ultraviolet light at an intensity that is sufficient to photochemically decay said compound but is nonlethal to the *Phanerochaete chrysosporium*;
   wherein step a and step b occur simultaneously.

2. The method of claim 1 further comprising the step of treating the medium with an antibiotic to inhibit the growth of competing microorganisms prior to contacting with the strain of *Phanerochaete chrysosporium*, wherein the strain of *Phanerochaete chrysosporium* is resistant to the antibiotic.

3. The method of claim 2 wherein the antibiotic is a fungicide.

4. The method of claim 3 wherein the fungicide is selected from the group comprising: benomyl, triforine, triadimifon, flusilazole and myclobutanil.

5. The method of claim 1 further comprising the step of acidifying the medium as is needed to prevent growth of competing organisms.

6. The method of claim 5 wherein the acidifying lowers the pH of the medium to about 4.0.

7. The method of claim 1 wherein the medium is an aqueous solution.

8. The method of claim 1 further comprising the step of adding a carbon source for the *Phanerochaete chrysosporium* to the medium as needed and in an amount effective to ensure the *Phanerochaete chrysosporium* degrades said compound.

9. The method of claim 1 further comprising the step of oxygenating the medium as needed and in an amount effective to ensure that the *Phanerochaete chrysosporiumm* degrades said compound.

10. The method of claim 1 wherein the ultraviolet light has a wavelength of between and including 254 nm and 300 nm.

11. The method of claim 1 wherein the fungi are attached to a solid support.

* * * * *